United States Patent [19]

Doane

[11] Patent Number: 4,919,651

[45] Date of Patent: Apr. 24, 1990

[54] CATHETER HAVING A DOUBLE LUMEN AND A BALLOON AND METHOD OF USING THE SAME FOR CONTROLLED OPERATIVE CHOLANGIOGRAPHY

[75] Inventor: Wilton A. Doane, Santa Barbara, Calif.

[73] Assignee: Santa Barbara Medical Foundation Clinic, Santa Barbara, Calif.

[21] Appl. No.: 296,360

[22] Filed: Jan. 9, 1989

Related U.S. Application Data

[63] Continuation of Ser. No. 183,408, Apr. 15, 1988, abandoned, which is a continuation of Ser. No. 729,977, May 1, 1985, abandoned.

[51] Int. Cl.⁵ .................................. A61M 29/00
[52] U.S. Cl. .................................. 604/96; 128/656; 128/658; 604/164; 606/194

[56] References Cited

U.S. PATENT DOCUMENTS

| | | | |
|---|---|---|---|
| 3,190,291 | 6/1965 | Foley | 604/98 |
| 3,394,705 | 7/1968 | Abramson | 604/43 |
| 3,467,101 | 9/1969 | Fogarty et al. | 128/348.1 |
| 3,769,981 | 11/1973 | McWhorter | 604/170 |
| 3,867,945 | 2/1975 | Long | 604/170 |
| 3,923,065 | 12/1975 | Nozick et al. | 128/348.1 |
| 3,954,110 | 5/1976 | Hutchinson | 604/102 |
| 3,977,408 | 8/1976 | MacKew | 604/102 |
| 4,044,757 | 8/1977 | McWhorter et al. | 128/655 |
| 4,044,758 | 8/1977 | Patel | 128/655 |
| 4,205,683 | 6/1980 | O'Neill | 604/99 |
| 4,263,917 | 4/1981 | Moss | 604/97 |
| 4,342,316 | 8/1982 | Rosenberg | 604/103 |
| 4,370,982 | 2/1983 | Reilly | 604/98 |
| 4,547,187 | 10/1985 | Kelly | 604/97 |

FOREIGN PATENT DOCUMENTS

| | | | |
|---|---|---|---|
| 2816391 | 11/1978 | Fed. Rep. of Germany | 128/658 |
| 0997657 | 2/1983 | U.S.S.R. | 128/656 |

Primary Examiner—C. Fred Rosenbaum
Assistant Examiner—Anthony M. Gutowski
Attorney, Agent, or Firm—Daniel J. Meaney, Jr.

[57] ABSTRACT

A catheter formed of a double lumen tubing having at one end thereof a distal tip and at least one opening extending from the interior of one lumen of the double lumen tubing to the exterior thereof and a plurality of second openings located a predetermined distance from at least one opening toward said other end thereof and extending from the interior of the other lumen of the double lumen tubing to the exterior thereof, a bifurcated connector located at said other end of the double lumen tubing, a first elongated tubing member operatively coupled to said bifurcated connector and communicating with said one lumen and a second elongated tubing member operatively coupled to said bifurcated connector which communicates with said other lumen and a balloon surrounding said one end of said double lumen tubing and enclosing said first openings with a removable elongated stylet located in the second passsageway and other lumen, is shown.

7 Claims, 2 Drawing Sheets

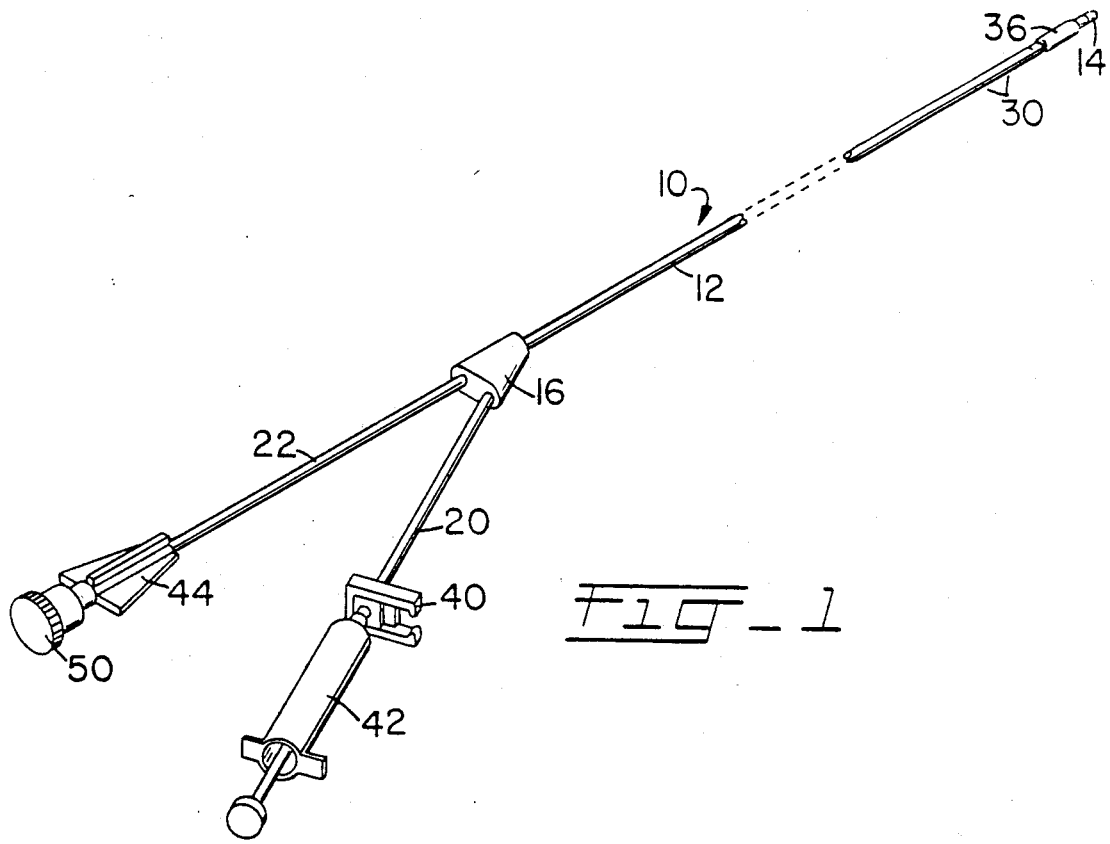
Fig_1
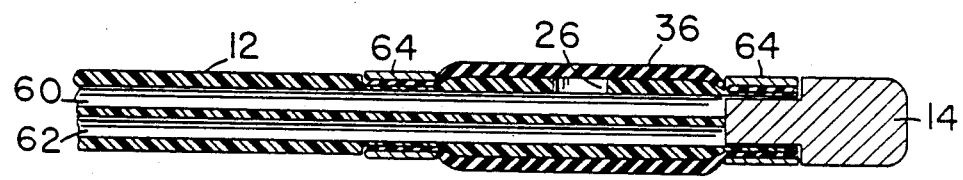
Fig_2
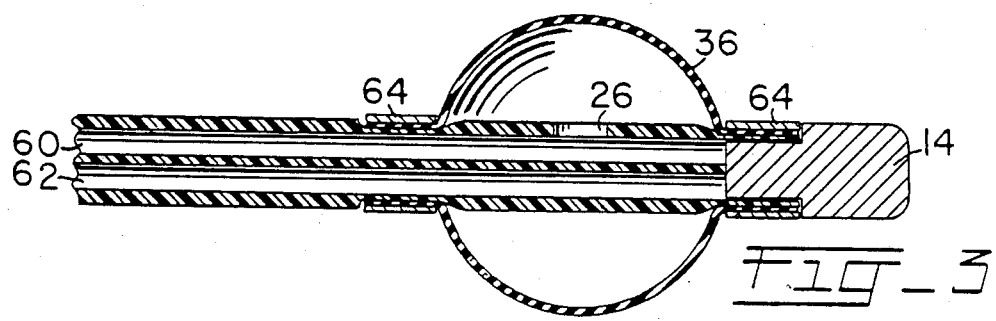
Fig_3

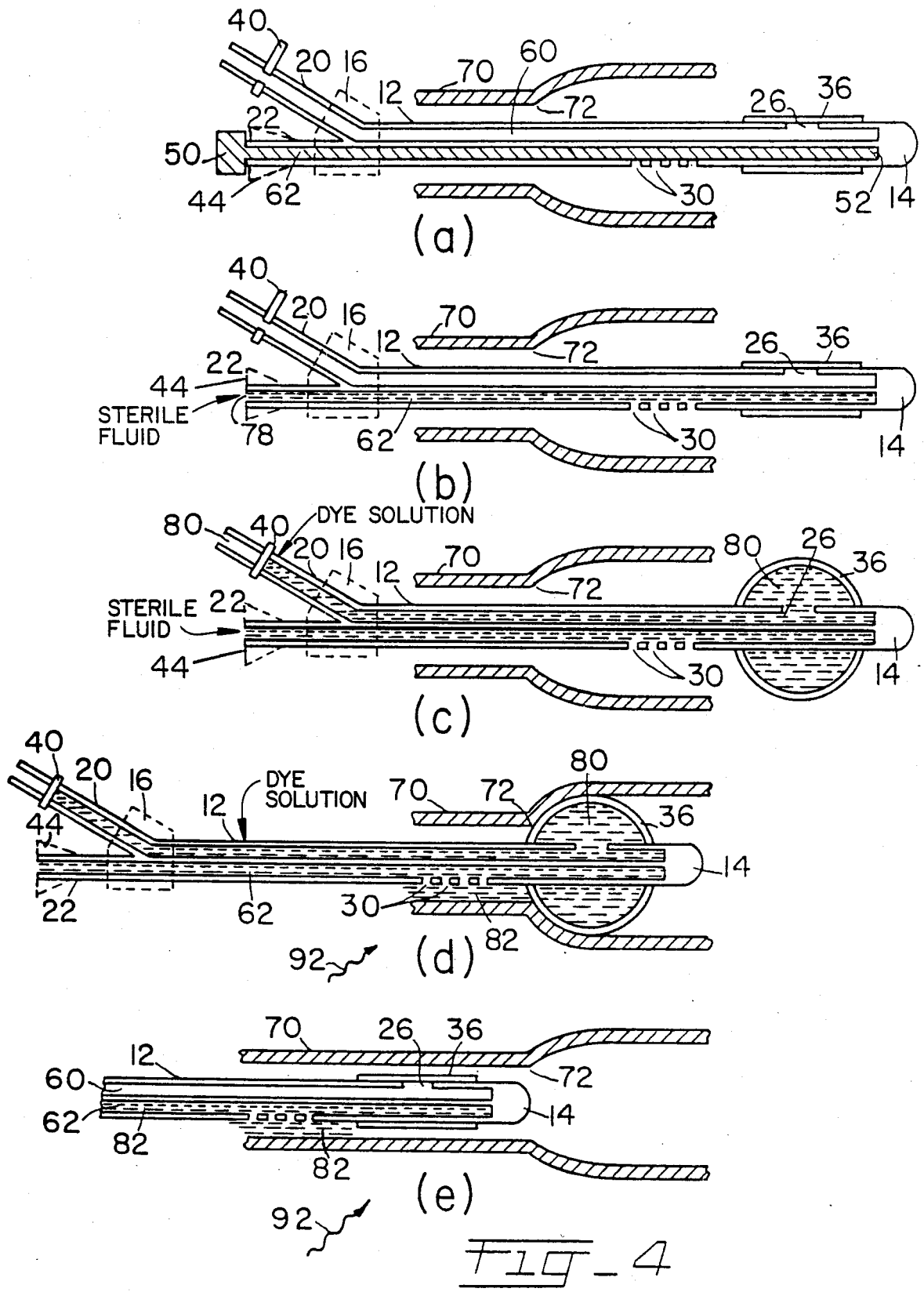
FIG_4

CATHETER HAVING A DOUBLE LUMEN AND A BALLOON AND METHOD OF USING THE SAME FOR CONTROLLED OPERATIVE CHOLANGIOGRAPHY

RELATED APPLICATIONS

This application is a continuation of application Ser. No. 07/183,408 filed Apr. 15, 1989, now abandoned, which is a continuation of application Ser. No. 06/729,977 filed May 1, 1985, now abandoned.

BACKGROUND OF THE INVENTION

1. Field of the Invention

This invention relates to a double lumen catheter having a balloon at one end thereof and a bifurcated inlet connector at the other end thereof which is adapted for use in conducting operative cholangiography. More specifically, the double lumen balloon catheter is adapted for use in and with a method for controlled filling of the biliary ductal system with a dilute dye for operative cholangiography.

2. Description of the Prior Art

Single lumen balloon catheters are known in the art. Typical of such known devices is a balloon catheter which is used for embolectomy purposes, and one such device is described in U.S. Pat. No. 3,435,826. In such use, a balloon catheter is inserted into and through a blood clot positioning the deflated balloon behind the pierced clot. The balloon is then inflated and the catheter is withdrawn urging the clot toward a known opening for removal.

Another known balloon catheter has a metal lumen formed of a wire coil which receives and guides a metal wire stylet within the catheter. One such device is disclosed in U.S. Pat. No. 3,467,101 wherein the c such device is disclosed in U.S. Pat. No. 3,467,101 wherein the catheter balloon is protected from puncture from the stylet by the structure of the device and the catheter has an improved tip construction to provide for a plurality of uses, such as thrombectomy, arterial embolectomy and other purposes. The disclosed single lumen balloon catheter has a valve for occluding fluid in the balloon.

An improved flow directed multilumen balloon catheter adapted to be passed freely through small arteries and veins is known in the art. A method of fabrication of one such catheter is disclosed in U.S. Pat. No. 3,634,924.

The surgical literature describes many different methods for practicing operative cholangiography and relates the inadequacy of clinical criteria in assessing the need for common bile duct exploration at the time of cholecystectomy. One reference of such known prior art is an article entitled "Common Duct Exploration For Stones," by F. Glenn which appeared in the *S.G. & O.* Volume 95, page 431 (1952).

SUMMARY OF THE INVENTION

This invention relates to a new, novel and unique catheter having a balloon and method of using a double lumen balloon catheter for controlled operative cholangiography. The double balloon catheter is adapted to be inserted into and proceeded along a natural passageway within the human body. In the preferred embodiment, the double lumen balloon catheter has a double lumen tubing which terminates in a distal tip at one end thereof and has a bifurcated connector at the other end thereof. The double lumen tubing has at one end adjacent the distal tip at least one opening extending from the interior of one lumen of the double lumen tubing to the exterior thereof and a plurality of second openings located a predetermined distance from at least one opening toward said bifurcated connector and extending from the interior of the other lumen of the double lumen tubing to the exterior thereof. The bifurcated connector has a first passageway which communicates with the one lumen and a first elongated tubing member, and a second passageway which communicates with the other lumen and a second elongated tubing member. A balloon surrounds the one end of the double lumen tubing and encloses the at least one opening. In addition, a valve having an open and closed position is operatively coupled to the first elongated tubing. When the valve is in the open position, it is adapted to have a fluid transported therethrough into the first elongated tubing through the at least one opening into expanding engagement with the balloon. The valve, when actuated from the open position to the closed position, is adapted to seal or occlude the diluted dye solution in the balloon at a selected expanded dimension.

In addition, a method for controllably filling a natural passageway terminating in a passageway opening in a human body with a dye fluid which is adapted to be responsive to x-rays during operative cholangiography comprising the steps of inserting into the natural passageway such a double lumen balloon catheter having a removable elongated stylet adapted to be inserted into the second elongated tubing and into said other lumen; guiding the double lumen catheter through the natural passageway and through the passageway opening a sufficient distance to transport the balloon beyond the passageway opening; removing the stylet from the second elongated tubing member and other lumen; urging a sterile fluid through the second elongated tubing member and bifurcated connector into the other lumen and through the plurality of second openings to remove any bubbles therein; urging the dye solution into said valve, through the first elongated tubing member through the bifurcated connector into the one lumen and through the at least one opening to expand the balloon to a selected expanded dimension; occluding the dye solution in the one lumen with a valve by placing the same in a closed position; withdrawing the catheter retrograde until the expanded balloon impinges and seals the opening; urging a dye solution into the said second elongated tubing member through the bifurcated connector into the other lumen through the plurality of second openings and into the natural passageway to inflate the same; and imaging the inflated natural passageway with x-rays. Additional steps of taking additional x-rays may be used.

The use of a double lumen tubing with a balloon at one end thereof and a bifurcated connector having two separate elongated tubes extending therefrom which communicate with the two lumens wherein one lumen is used to inflate the balloon with a fluid and to occlude the same with a valve and wherein the other lumen is used to pass a fluid into a natural passageway having a passageway opening in a human body, is not known in the prior art. In addition, the invention and method described herein is not suggested or disclosed either by the known prior art included in the surgical literature and is not anticipated thereby.

One advantage of the present invention is that the double lumen catheter can easily be used in controlled operative cholangiography. Specifically, the present invention enables a surgeon to obtain controlled filling of the biliary ductal system with a diluted dye solution to improve the visualization of the common bile duct and common hepatic duct during an operative cholangiography procedure.

Another advantage of the present invention is that the double lumen balloon catheter can be inserted into a natural passageway and syringes can be used to urge sterile fluids and diluted dyes into the double lumen catheter during use thereof.

Yet another advantage of the present invention is that the balloon can be inflated by use of a fluid, such as a dye, and the inflated or expanded balloon withdrawn against the passageway opening to block off the same enabling a fluid, such as the same diluted dye, to inflate the natural passageway. This has direct application and use in controlled operative cholangiography.

BRIEF DESCRIPTION OF THE DRAWING

These and other advantages and objects of the present invention and method can be easier understood by reference to the following description of the preferred embodiment which includes the following figures:

FIG. 1 is a perspective view of a double lumen balloon catheter of the present invention;

FIG. 2 is a partial end view in cross-section showing the double lumen tubing construction, the balloon and distal tip with the balloon in a deflated position;

FIG. 3 is a partial end view in cross-section showing the double lumen catheter with the balloon expanded to a selected expanded dimension; and FIGS. 4(a) to 4(e), inclusive, are diagrammatic views showing the various steps for using the catheter during controlled operative cholangiography.

DESCRIPTION OF THE PREFERRED EMBODIMENT

In the preferred embodiment, as illustrated in FIG. 1, the catheter generally shown as 10 has a double lumen tubing 12 which terminates in a distal tip 14 at one end thereof. The other end of the double lumen tubing 12 terminates in a bifurcated connector which, in the preferred embodiment, is a bifurcated wye connector 16. A first elongated tubing member which, in the preferred embodiment, is an elongated plastic tube 20 is operatively connected to the bifurcated connector 16. A second elongated tubing member in the form of an elongated extruded tube 22 is operatively connected to the other side of the bifurcated connector 16. The elongated tube 20 communicates with one lumen of the double lumen tubing while the other elongated tubing 22 communicates with the other lumen of the double lumen tubing.

The one end of the double lumen tubing which is adjacent to the distal tip has at least one opening extending from the interior of one lumen of the double lumen tubing to the exterior thereof. This is illustrated in FIG. 2 as opening 26. In addition, a plurality of second openings 30 are located a predetermined distance from the at least one opening 26 toward the bifurcated connector 16. The second openings 30 extend from the interior of the other double lumen tubing to the exterior thereof. The bifurcated connector 16 has a first passageway which essentially connects the one lumen to the elongated tubing 20 and a second passageway which connects the other lumen of the double lumen tubing to the elongated tube 22.

A balloon surrounds the one end of the double lumen tubing 12 and encloses the at least one opening 26. The construction and means for connecting the balloon 36 to the double lumen tubing 12 is illustrated in FIGS. 2 and 3.

The elongated tubing 20 which extends from the bifurcated connector 16, is terminated in a valve 40 which has an open and closed position. The valve 40 is operationally coupled to the elongated tubing member 20 which communicates with the first passageway and the bifurcated connector 16. The valve 40, when in an open position, is adapted to enable a fluid to be transported therethrough into the elongated tubing member 20, which is in communication with the first passageway in the bifurcated connector 16, through the one lumen of the double lumen tubing 12 and through said at least one opening 26 into expanding engagement with the balloon 36. When the valve 40 is actuated from an open position to a closed position, the fluid contained in the elongated tubing, the bifurcated connector 16, the one lumen of the double lumen tubing 12 and the balloon 36 is occluded to hold the balloon 36 at a selected expanded dimension. Valve 40 includes means for operatively coupling a syringe 42 containing a fluid thereto to enable urging of the fluid from the syringe 42 through the valve 40.

An inlet 44 is operatively coupled to the other elongated tubing 22 which is connected to the second passageway in the bifurcated connector 16. The inlet 44 is adapted to enable a fluid to be passed therethrough to the other lumen, through the second openings 30 and to the exterior of the double lumen tubing 12.

A removable elongated metal wire stylet 50 is adapted to be inserted into the inlet 44. When in the inserted position, the elongated metal wire stylet 44 is inserted into the inlet 44 through the second passageway in the bifurcated connector 16 and into the other lumen of the double lumen tubing 12. The stylet has a sufficient length to enable the end thereof to extend into the other lumen 62 to approximately the distal tip 44.

FIG. 2 shows in detail the construction in the vicinity of the one end of the double lumen catheter 12. The distal tip 14 is located at one end of the double lumen catheter 12 and terminates both the one lumen 60 and the other lumen 62 defining the double lumen catheter. The balloon 36 is secured at the opposite ends thereof by securing means 64 and are on the opposite ends of the balloon 36 such that the balloon material is stretched longitudinally between the securing means 64 over the at least one opening 26, and the balloon material 36 is held snugly against the double lumen tubing 12 exterior when the balloon 36 is deflated.

FIG. 3 shows the construction when the balloon is expanded, due to a fluid being urged therein. The balloon 36 is expanded by the transportation of a fluid in the one lumen 60 through the at least one opening 26 causing the balloon 36 to expand to a selected expanded dimension.

FIGS. 4(a) through 4(e) show the use of a double lumen balloon catheter for controllably filling a natural passageway 70 in a passageway opening in a human body with a dye fluid which is adapted to be responsive to x-rays during operative cholangiography. In FIG. 1, the step of inserting the double lumen catheter 12 having a distal tip 14 on one end thereof into the natural passageway 70, is shown in FIG. 4(a). The stylet 50 has the metal wire portion thereof 52 illustrated diagrammatically in FIG. 4(a). The distal tip is inserted into the natural passageway 70, which may be a common bile duct which terminates in the ampulla of Vater. Thus, the double lumen catheter 12 is guided through the natural passageway 70 and through and beyond a passageway opening 72 of the natural passageway 70 a sufficient distance to transport the balloon 26 beyond the passageway opening 72.

The next step is the removing of the stylet 50 to withdraw the metal wire 52 from the second elongated tubing 22 and the other lumen 62. The then next step is the urging of a sterile fluid 78 through the second elongated tubing member 22 and bifurcated connector 16 into the other lumen 62 and through the second openings 30 to remove any bubbles therein. This is illustrated in FIG. 4(b).

The further step is the urging of a diluted dye solution through the open valve 40 and through the first elongated tubing member 20 and the bifurcated connector 16 into the one lumen 60 and through the at least one opening 26 to expand the balloon 36 to a selected expanded dimension.

The next step is the occluding of the diluted dye solution in the one lumen 60 with the valve 40 by placing the valve 40 in a closed position, as shown in FIG. 4(a). This has the effect of sealing the fluid 80 within the first elongated tubing member 20, the one lumen 60 of the double lumen tubing 12, the at least one opening 26, and the interior of the expanded balloon 36.

The further step is the withdrawing in retrograde of the catheter 12 until the expanded balloon impinges and seals the passageway opening 72, as illustrated in FIG. 4(d). Thereafter, the next step is the urging of a dye solution 82 into the second elongated tubing means 22, through the bifurcated connector 60, into the other lumen 62, through the second openings 30 into the natural passageway 70 to inflate the same. The periphery of the balloon 36 seals the passageway opening 72 to enable the natural passageway 70 to be inflated.

Thereafter, the step of imaging the inflated natural passageway and dyes with x-rays 92 is conducted and the images developed using normal techniques.

The next step is aspirating the balloon 36 to deflate the same and withdrawing the catheter 12 retrograde until the balloon 36 is within the natural passageway 70. The next step is urging additional dye 82 into the natural passageway 70 through the second elongated tubing member 22, the bifurcated connector 16 and the other lumen 62 and plurality of second openings 30. Thereafter, the step of imaging the inflated natural passageway 70 with x-rays 92 is conducted and the images developed.

The double lumen balloon catheter disclosed herein and the method of using the same for controlled operative cholangiography enables a surgeon to perform surgery using a technique which was heretofore not known.

What is claimed is:

1. A system for controllably filling a natural passageway terminating in a passageway opening in a human body with a dye fluid which is adapted to be responsive to x-rays during operative cholangiography, said system comprising a cholangiography catheter comprising a flexible double lumen tubing having at one end thereof a first opening extending from the interior of one lumen of the double lumen tubing to the exterior thereof and at the other end thereof a plurality of second openings located a predetermined distance from the first opening, said plurality of second openings extending from the interior of the other lumen of the double lumen tubing to the exterior thereof;

a closed, fluid tight distal tip located at said one end of the double lumen tubing;

a bifurcated connector located at said other end of the double lumen tubing, said bifurcated connector having two separate passageways therethrough so as to communicate with the two tubing members and lumens respectively;

a first elongated tubing member operatively coupled to said bifurcated connector which communicates with said one lumen and a second elongated tubing member operatively coupled to said bifurcated connector which communicates with said other lumen;

a balloon having opposed ends surrounding said one end of said double lumen tubing and enclosing said first opening;

means for securing the opposed ends of the balloon to said double lumen tubing exterior with the balloon material stretched longitudinally between said securing means over said first openings and snugly against the double lumen tubing exterior when the balloon is deflated; and a valve having an open and closed position operatively coupled to said first elongated tubing member, said valve when in said open position enables a fluid to be transported therethrough into said first elongated member, through said first opening into expandable engagement with said balloon, said valve when actuated from said open position to said closed position occludes fluid in said one lumen and to hold said balloon at a selected expanded direction;

an inlet operatively coupled to the elongated tubing member and which enables a fluid to be passed therethrough into said other lumen, through said second openings, to the exterior of said double lumen tubing and into a natural passageway;

a removable elongated stylet positioned to extend through said second elongated tubing communicating with the second passageway through said bifurcated connector, through said second passageway and through said other lumen, said stylet having a length to enable the end thereof to extend into said other lumen to the distal tip to stiffen said flexible double catheter and render the same relatively rigid without stretching the same, said stylet being insertable into the catheter stiffening the same when the catheter is inserted into and proceeded along the common bile duct to the ampulla of vater within the human body and being removeable when the catheter is in the ampulla of vater;

a source of sterile fluid alternatively attached to said inlet to urge a sterile fluid through said second elongated tubing member and said bifurcated connector into said other lumen and through said second openings to remove any bubbles therefrom;

a source of a dye solution alternatively coupled to said valve for selectively urging a dye solution into said one lumen and through said first opening to expand said balloon to a selected expanded diameter and into said other lumen through said second openings and into the natural passageway to inflate the same; and a source of x-rays for imaging the inflated natural passageway with x-rays.

2. The system of claim 1 wherein the catheter is made of a plastic material.

3. The system of claim 1 wherein said plurality of second openings in the catheter comprises four spaced openings.

4. The system of claim 1 wherein said bifurcated connector is Wye-shaped and said first and second elongated tubing members are formed of a plastic material.

5. The system of claim 1 wherein said valve includes means for operatively coupling thereto a syringe containing a fluid to enable urging of a said fluid from said syringe through said valve.

6. A method for controllably filling a natural passageway terminating in a passageway opening in a human body with a dye fluid which is adapted to be responsive to x-rays during operative cholangiography comprising the steps of inserting into a said natural passageway a flexible double lumen catheter having a close, fluid tight distal tip at one end thereof and a bifurcated connector at the other end thereof wherein said one end has adjacent said distal tip a first opening extending from the interior of one lumen of the double lumen tubing to the exterior thereof which is surrounded by a deflated balloon enclosing said first opening and a plurality of second openings located a predetermined distance from the at least one opening and extending from the interior of the other lumen of the double lumen tubing to the exterior thereof and wherein said bifurcated connector has a first passageway which communicates with said one lumen and a first elongated tubing member and a second passageway which communicates with said other lumen and a second elongated tubing member, and a valve having an open and closed position operatively coupled to the first elongated tubing member, said double lumen catheter having a removable elongated stylet therein which extends into said second elongated tubing member to stiffen said flexible double lumen catheter and render the same relatively rigid without stretching the same, said second passageway and into said other lumen;

guiding said flexible double lumen catheter stiffened by said removable elongated stylet through a said natural passageway into said passageway opening a sufficient distance to transport said balloon beyond said passageway opening;

removing the elongated stylet from said second elongated tubing member, said bifurcated connector and said other lumen rendering said other lumen to be unobstructed to freely pass fluid therethrough;

urging a sterile fluid through said second elongated tubing member, bifurcated connector into said other lumen and through said second openings to remove any bubbles therein;

urging a dye solution into said valve, through said first elongated tubing member, through said bifurcated connector into said one lumen and through said first opening to expand said balloon to a selected expanded dimension;

occluding the dye solution in the one lumen with a valve wherein the valve is placed in a closed position;

withdrawing the catheter retrograde until the expanded balloon impinges and seals the passageway opening;

urging a dye solution into said second elongated tubing member, the bifurcated connector, into the other lumen, through the second openings and into the natural passageway to inflate the same; and imaging the inflated natural passageway and inflated balloon with x-rays.

7. The method of claim 6 further comprising the steps of aspirating the balloon to deflate the same and withdrawing the catheter retrograde until the balloon is within the natural passageway;

urging additional dye into said natural passageway through said second elongated tubing member, said bifurcated connector, said other lumen and a plurality of second openings; and imaging the natural passageway with x-rays.

* * * * *